US008926095B2

(12) United States Patent
Bartels

(10) Patent No.: US 8,926,095 B2
(45) Date of Patent: Jan. 6, 2015

(54) INEXPENSIVE DEVICE AND METHOD FOR CONNECTING A CAMERA TO A SCOPE FOR PHOTOGRAPHING SCOPED OBJECTS

(71) Applicant: David P. Bartels, Amherst, NY (US)

(72) Inventor: David P. Bartels, Amherst, NY (US)

(*) Notice: Subject to any disclaimer, the term of this patent is extended or adjusted under 35 U.S.C. 154(b) by 0 days.

(21) Appl. No.: 13/862,722

(22) Filed: Apr. 15, 2013

(65) Prior Publication Data

US 2013/0293840 A1 Nov. 7, 2013

Related U.S. Application Data

(60) Provisional application No. 61/624,474, filed on Apr. 16, 2012.

(51) Int. Cl.
*A61B 3/14* (2006.01)

(52) U.S. Cl.
USPC .......................................... 351/206; 351/208

(58) Field of Classification Search
USPC .................................................. 351/200–246
See application file for complete search history.

(56) References Cited

U.S. PATENT DOCUMENTS

| 7,465,049 | B2 * | 12/2008 | Maeda et al. | ................. 351/205 |
| 7,901,078 | B2 | 3/2011 | Niven | |
| 8,262,221 | B2 * | 9/2012 | Filar | ............................ 351/206 |
| 2009/0259127 | A1 | 10/2009 | Ehrecke | |
| 2012/0320340 | A1 * | 12/2012 | Coleman, III | ................ 351/208 |

OTHER PUBLICATIONS

Telscreen, "Telscreen's EyeRes Digital Imaging System," World Wide Web page, Feb. 2010 ed, pp. 1 (and home page).
Keeler, "Keeler Portable Slit Lamp iPhone 4 Imaging Adapter," World Wide Web page, pp. 1, at least as early as Feb. 15, 2012.
Keeler, "iPhone Connect Demo," World Wide Web pages, pp. 1-2, Feb. 27, 2011 (date uploaded to www.youtube.com).

* cited by examiner

*Primary Examiner* — Mohammed Hasan
(74) *Attorney, Agent, or Firm* — James C. Simmons

(57) ABSTRACT

A device and method for connecting a camera to a scoping apparatus for viewing and taking photos of an eye-ball or other object imaged by the scoping apparatus. A case receives a compact high-resolution camera, and an attachment is connected to the case. The attachment is detachably connected to an eye-piece of the scoping apparatus in a manner to allow passage of an image from the scoping apparatus through the device to the camera for viewing and taking of photos thereof. A sleeve portion of the attachment and the eye-piece have generally the same diameter to allow the attachment sleeve to be fitted over the eye-piece. When the attachment sleeve and eye-piece have different diameters, an adapter having a generally cylindrical shape and a thickness equal generally to the difference in thicknesses is received on the eye-piece and the attachment sleeve received on the adapter to couple the attachment to the eye-piece.

20 Claims, 3 Drawing Sheets

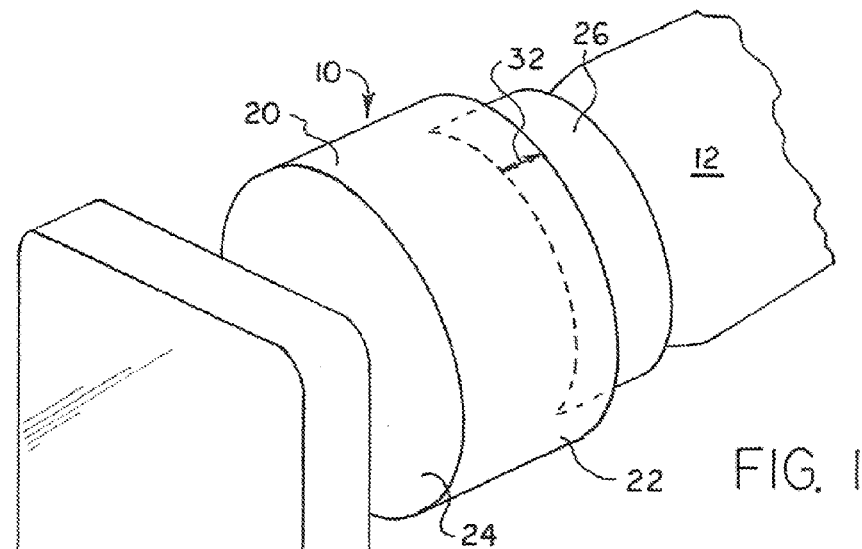
FIG. 1
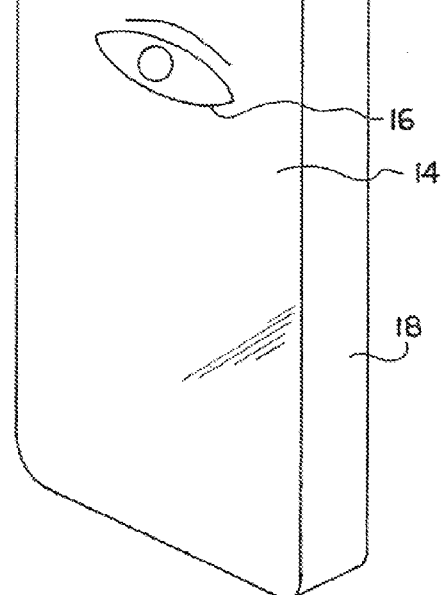
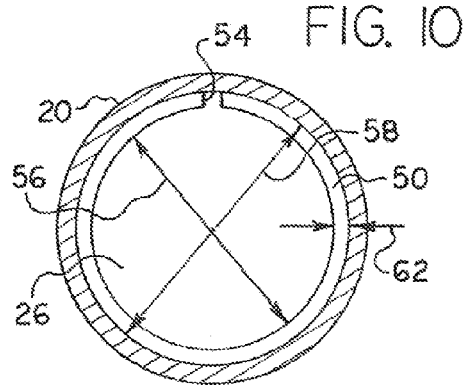
FIG. 10
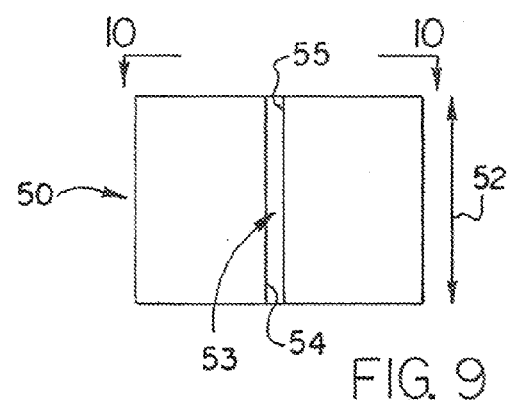
FIG. 9

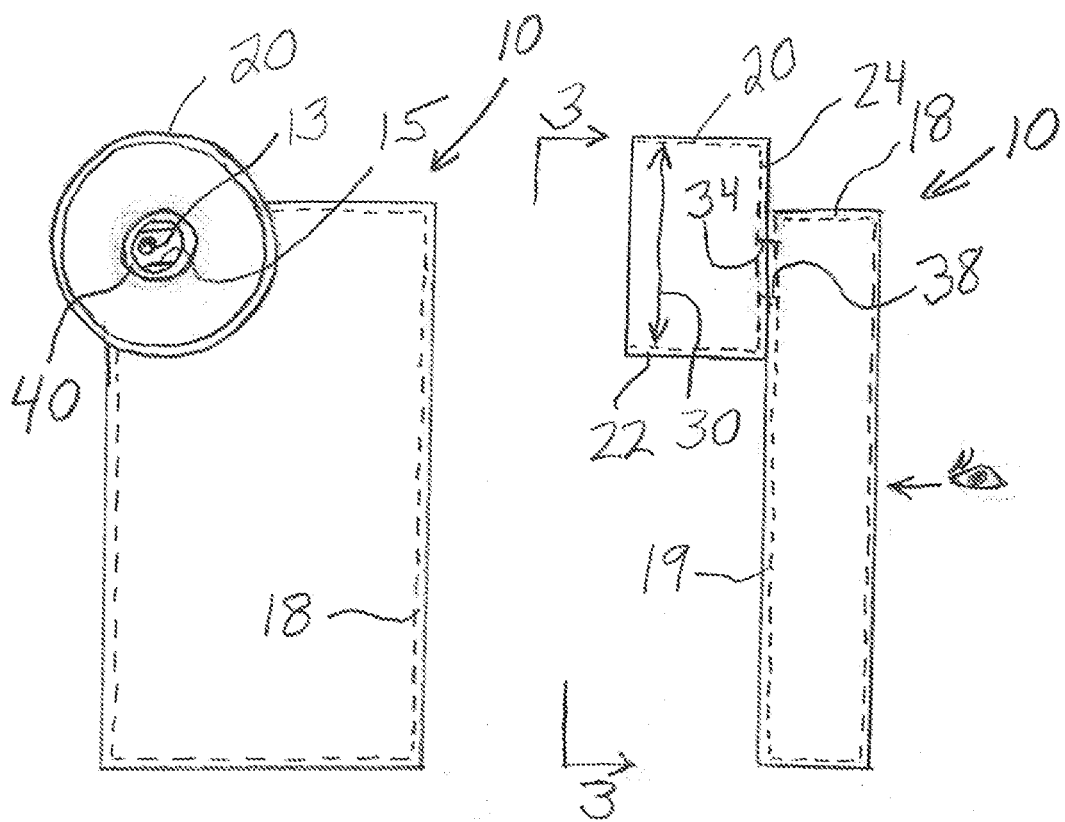
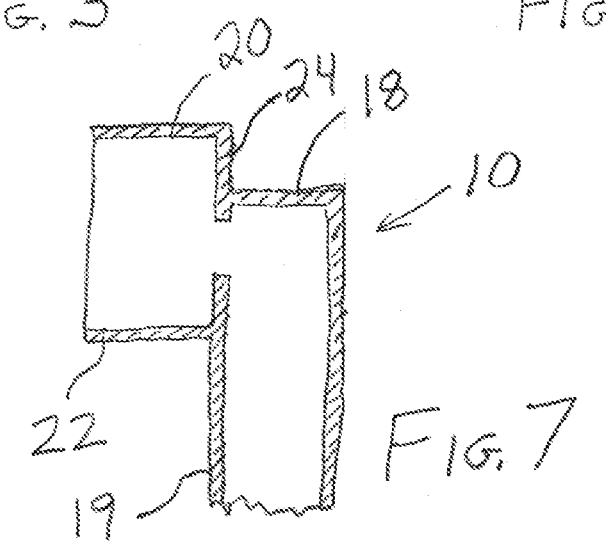

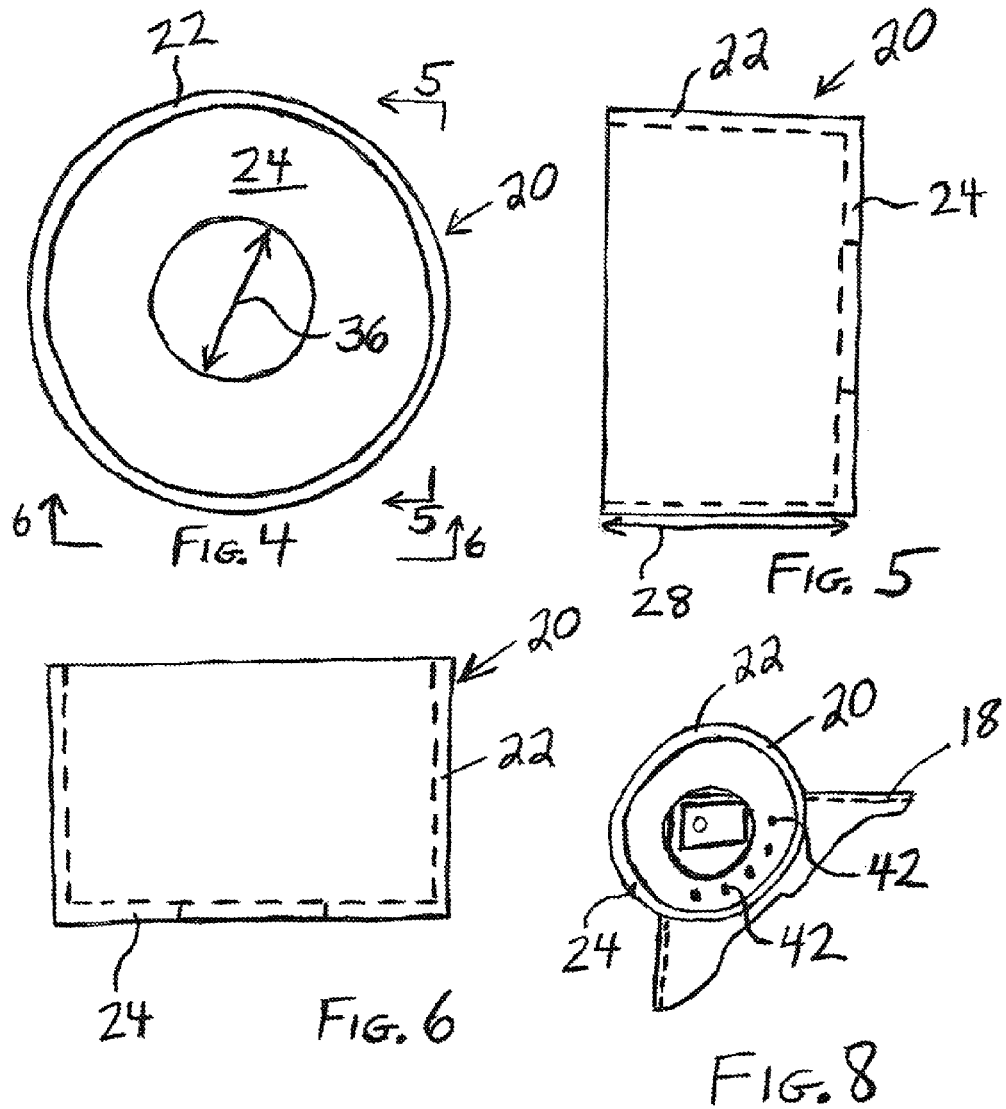

INEXPENSIVE DEVICE AND METHOD FOR CONNECTING A CAMERA TO A SCOPE FOR PHOTOGRAPHING SCOPED OBJECTS

CROSS REFERENCE TO RELATED APPLICATION

Priority of U.S. provisional application 61/624,474, filed Apr. 16, 2012, which is incorporated herein by reference, is hereby claimed.

BACKGROUND OF INVENTION

The present invention relates generally to the field of cameras and optics. More particularly, the present invention relates to the taking of photos and/or moving pictures of scoped or imaged objects such as microscopic or bio-microscopic views, for example, a bio-microscopic view of a person's eye-ball.

U.S. Pat. No. 7,901,078 and U.S. published application 2009/0259127, which are hereby incorporated herein by reference, contain discussions of imaging apparatus/bio-microscope which may be of interest to the present invention.

When an eye-ball is viewed through a bio-microscopic, a camera may be connected therewith to take photos and/or videos thereof. TelScreen, a division of Micro-Med, Inc., of Louisville, Ky., manufactures and markets ophthalmoscopes, which are well known in the art, and also manufactures and markets such digital imaging hardware and software providing high quality photos and videos, but at a cost which may be on the order of $10,000 to $15,000.

It is accordingly an object of the present invention to provide an inexpensive, light weight, and convenient and easy-to-use means for making high quality photos and/or videos of a scoped eye-ball or other object.

In order to provide such an inexpensive, light weight, and convenient and easy-to-use means, a cover for a compact high resolution camera (or compact iPhone or other phone incorporating the camera) is coupled to an attachment in the form, at least in part, of a cylindrical opaque sleeve for being easily and securely received over an eye-piece of an imaging tool or scoping device to allow the camera to be attached thereto for receiving images therefrom and taking photos and/or videos thereof.

The above and other objects, features, and advantages of the present invention will be apparent in the following detailed description of the preferred embodiment(s) thereof when read in conjunction with the appended drawings wherein the same reference numerals depict the same or similar parts throughout the several views.

BRIEF DESCRIPTION OF THE DRAWINGS

FIG. 1 is a perspective view of a camera device (iPhone incorporating a camera) in accordance with the present invention, shown connected to a bio-microscope (shown partially) for taking photos/videos of an eye-ball as imaged by the bio-microscope.

FIG. 2 is a side elevation view of an iPhone cover and an attachment for connecting the camera to the bio-microscope (the means of connecting the cover to the attachment not shown for purposes of clarity).

FIG. 3 is an elevation view thereof taken along lines 3-3 of FIG. 2 and illustrating a means of connecting the cover to the attachment.

FIG. 4 is a rear view of the attachment.

FIG. 5 is a side view of the attachment taken along lines 5-5 thereof.

FIG. 6 is a side view of the attachment taken along lines 6-6 thereof.

FIGS. 7 and 8 are partial views similar to that of FIG. 3 illustrating respective alternative means of connecting the cover to the attachment.

FIG. 9 is a side view of an adapter for attaching the attachment to the bio-microscope eye-piece, for use when the attachment inner diameter does not match the eye-piece diameter.

FIG. 10 is an end view, taken along lines 10-10 of FIG. 9, of the adapter, illustrating the adapter coupling the eye-piece to the attachment, wherein the attachment is shown in cross-section.

DETAILED DESCRIPTION OF THE PREFERRED EMBODIMENT(S)

Referring to FIG. 1, there is illustrated generally at 10 a device connected to a bio-microscope 12 (shown partially, a bio-microscope being well known in the art) for receiving images therefrom and transmitting them to a compact camera (preferably including a video camera as well as a still picture camera, each camera being preferably high resolution), illustrated generally at 13 (FIG. 3), which may be (but is not required to be) conventionally built into a portable or cellular preferably compact digital phone 14, which is well known in the art, so that high quality photos and/or videos may be taken thereof. While the phone 14 itself is not shown in FIG. 3, the camera portion (shutter eye for passage of the image 16 to the lens) 13 and a conventional recess 15 in the phone therefor are illustrated for the purposes of clarity of illustration.

By "high resolution" is meant, for purposes of this specification and the claims, for still pictures a resolution of 2 megapixels or higher, preferably at least 5 megapixels, and for video a resolution of 480p or higher, more preferably 1080p or higher. 720p and 1080p refer to a progressive HDTV signal with 720 and 1080 respectively horizontal lines and an aspect ratio of 16:9, the letter p standing for progressive scan or non-interlaced.

By "compact" is meant, for purposes of this specification and the claims, a length of about 5 inches or less, a width of about 2½ inches or less, and a thickness of about ½ inch or less, for example, about 4½ inches×2¼ inches×⅜ inch (which are typical dimensions of an older iPhone4), and, for another example, about 4.87 inches (123.8 mm)×2.31 inches (58.6 mm)×0.3 inch (7.6 mm) (which are believed to be the dimensions of the newer iPhone5).

The phone 14 is preferably an internet-enabled and multi-media-enabled smartphone (which is a mobile computing platform and has more advanced computing ability and connectivity than a feature phone), more preferably an iPhone such as, for example, an iPhone3GS (video recording at 480p), an iPhone4 (video recording at 720p), an iPhone4S (8 megapixel with video recording at 1080p), and the newer iPhone5, produced by Apple Inc., and including more advanced models of compact cameras and/or smartphones and/or iPhones as may be produced hereinafter. An image produced by such an iPhone is illustrated at 16. Examples provided in this application are for illustrative purposes only and not for purposes of limitation. The present invention is meant to include the fitting or coupling of any suitable camera to any suitable scoping device in accordance with the present invention as described hereinafter.

Referring to FIGS. 2 and 3, the phone 14 which includes the camera 13 is conventionally receivable in a thin-walled (for example, 1/64 to 3/32 inch, and defined herein, for the purposes of the claims and the specification, as having walls which are less than about 1/8 inch thick) protective cover 18 composed of clear plastic or other suitable material, conventionally supplied by Apple Inc. in connection with its supply of iPhones or otherwise conventionally supplied corollary to the sale of iPhones or may be supplied by another company in connection with or corollary to the sale of other suitable phones. The cover 18 may be a conventional phone cover or it may be specially made such as with upper and/or front openings so that the phone can be easily and quickly slid into and out of the cover and/or the image is not interfered with by the cover.

In order to couple the phone 14 (or other suitable camera device) to a scoping device or imaging tool such as, for example, the eye bio-microscope 12 (as seen in FIG. 1) for the taking of suitable high resolution bio-microscopic eye images 16, in accordance with the present invention, the device 10 includes an attachment 20 which is suitably connected to a wall, illustrated at 19, of the cover 18 in any of various alternatives three of which are discussed hereinafter with respect to FIGS. 3, 7, and 8 respectively. The device 10 thus includes the attachment 20 and the cover 18. However, it should be understood that the attachment 20 may be detachable from the cover 18 so that the attachment 20 and cover 18 may, if desired, be sold separately. While illustrated herein with respect to coupling of a camera device to an eye bio-microscope, it should be understood that the present invention may be used with other scoping devices or apparatus or imaging tools for transmissions of images to the camera device.

The attachment 20 is composed of a suitable material such as a suitable opaque (does not allow light to pass through) elastomeric material such as, for example, polypropylene, and includes a sleeve portion 22 in the form of a thin (for example, 1/64 to 3/32 inch) cylindrical wall one end of which is open and the other end of which is closed by a similarly thin planar wall 24 which is preferably integral therewith.

The sleeve wall 22 is cylindrical to fit the shape of a conventionally cylindrical eye-piece 26 of the bio-microscope and sized as well as being suitably rigid to snugly fit onto the eye-piece 26 for secure coupling thereto thus to allow passage of the image 16 from the eye-piece along the length, illustrated at 28 (FIG. 5), of the cylindrical wall 22. For example, the cylindrical wall 22 composed of polypropylene or other suitable material may have a thickness of about 1/32 inch and a length 28 of preferably about 1 inch or more, as suitable for the length of the eye-piece 26 to achieve a snug and secure fit. The cylindrical wall 22 has an inner diameter, illustrated at 30 (FIG. 2), which may equal substantially the diameter of the eye-piece it is to be used with, such as, for example, about 1½ inches to equal substantially the diameter of many typical bio-microscope eye-pieces, or about 1¼ inches to equal substantially the diameter of other typical bio-microscope eye-pieces. Bio-microscope eye-pieces currently typically have these two standard diameters of 1¼ and 1½ inches. However, the sleeve 22 may be made in a standard size, such as sized to have a wall diameter 30 of, for example, 1¼ inch and one or more adapters provided, as discussed hereinafter with respect to FIGS. 9 and 10, so that the sleeve can fit higher diameter eye-pieces such as those having 1½ inch diameters and perhaps others having larger diameters. For use, the sleeve 22 may be fitted onto the eye-piece 26 over a distance, illustrated at 32 (FIG. 1), of about 3/4 inch or otherwise a desired distance 32 to achieve the desired secure coupling with the desired rigidity. It should of course be understood that the sleeve wall 22 may have a shape other than cylindrical to fit an eye-piece 26 whose wall is non-cylindrical.

In order to allow passage of the image 16 to the shutter eye/lens 13, a suitably sized and positioned aperture or opening or cut-out 34 is provided in the attachment wall 24, generally centrally thereof, and is suitably positioned in alignment with the shutter eye/lens 13 when the camera/phone 14 is suitably received in the cover 18 and with sufficient dimension to allow passage of the image 16 to the lens 13. For example, the opening 34 may be (but is not required to be) circular and have a diameter, illustrated at 36, of, for example, about 1/4 inch. The cover 18 may have a corresponding cut-out or opening, illustrated at 38, in its wall 19 to prevent interference by the cover 18 with the passage of the image 16 to the shutter eye/lens 13, as is conventional, and this opening 38 may be similarly or differently sized and shaped than the opening 34. Thus, the openings 34 and 38 are provided so that both the attachment 20 and cover 18 desirably provide no interference with the passage of the image 16 from the bio-microscope 12 to the camera shutter eye/lens 13.

The attachment 20 is suitably connected to the cover wall 19 in any suitable manner. Preferably, as illustrated in FIG. 7, the attachment 20 and cover 18 are molded as a unit so that they are integral. Alternatively, as illustrated in FIG. 3, the attachment 20 and cover 18 are securely connected by a grommet, illustrated at 40, which is received in the openings 34 and 38 and stamped. In accordance with yet another embodiment, as illustrated in FIG. 8, the attachment 20 and cover 18 are securely connected by a suitable number of rivets, illustrated at 42. As previously discussed, the attachment 20 may be suitably detachable from the cover 18. It should of course be understood that any other suitable means for connecting the attachment 20 and cover 18 are meant to come within the scope of the present invention.

While the attachment 20 may be produced in a number of sizes to fit a number of eye-pieces 26 respectively of different diameters, in order to further reduce the manufacturing cost so as to keep the price to consumers low, the attachment 20 may be produced in a single standard size (sleeve diameter 30) to fit the diameter of the typically smaller eye-piece. Referring to FIGS. 9 and 10, in order to fit such a standard diameter attachment 20 to eye-pieces 26 having diameters larger than such a standard diameter, in accordance with a preferred embodiment of the present invention, an adapter, illustrated at 50, in the form of a sleeve is provided to be receivable between the attachment 20 and eye-piece 26. In order to provide ease of fitting the adapter 50 onto the eye-piece 26, the adapter 50 is slit longitudinally over the entirety of its length 52, as illustrated by slit 53 defining a gap. Thus, the adapter 50 has a form of a rectangular member curved onto itself to have the form of a sleeve. Thus, the adapter 50 has a cylindrical shape with a gap 53 defined by a pair of facing unconnected edges 54 and 55 which allows said adapter to be pulled apart enough circumferentially to be received on the eye-piece, then to spring back into engagement with the eye-piece. The sleeve length 52 may be, for example, 1 inch or as otherwise suitable. The sleeve inner diameter, illustrated at 56, is equal substantially to the eye-piece diameter so that the sleeve 50 can be securely fitted onto the eye-piece 26. The sleeve 50 is composed of a suitable plastic or other suitable material with elasticity to allow it to be opened up along the slit or gap 53 sufficiently to allow it to be suitably positioned onto the eye-piece 26 and can spring back into position engaging the eye-piece. The sleeve outer diameter, illustrated at 58, when fitted onto the eye-piece, is equal substantially to the attachment inner diameter 30 so that the attachment 20 can be securely fitted onto the sleeve 50 thereby to provide a secure connection of the attachment 20 to the eye-piece 26. Since eye-pieces 26 typically come in diameters of 1¼ inch and 1½ inch, the thickness, illustrated at 60, of the adapter 50 may, for example, be ¼ inch (1½ inch less 1¼ inch) so that an attachment 20 having a diameter 30 of 1¼ inch may be made to fit not only an eye-piece 26 having a diameter of 1¼ inch but also an eye-piece 26 having a diameter of 1½ inch by the use of an adapter 50 having a thickness 62 of ¼ inch. Of course, adapters 50 may have various outer diameters 58 and thus various thicknesses 62 to accommodate eye-pieces 26 having various diameters larger than diameter 56 respectively.

The size of an iPhone4 cover may, for example, approximately be an outer length of 4⅝ inches, an outer width of 2⅜ inches, and an outer thickness of ½ inch, with the walls thereof being about 1/32 inch thick. Of course, covers for other cameras or phones with cameras may have differing dimensions to fit the dimensions thereof.

It should be easily recognizable that the device 10 is provided to be inexpensively produced and of light weight and so that it can be easily and quickly and securely and conveniently attached to an bio-microscope eye-piece 26 or other suitable scoping eye-piece by merely slipping the sleeve 22 securely over the eye-piece 26. With the camera/phone received within the cover 18 and the sleeve slipped securely over the eye-piece 26, this allows the camera to be held securely in position so that the hands are conveniently free for movement of the bio-microscope or as otherwise needed. The eye can thus be conveniently viewed and the camera/phone held steady as the eye is being photographed/filmed.

It should be understood that, while the present invention has been described in detail herein, the invention can be embodied otherwise without departing from the principles thereof, and such other embodiments are meant to come within the scope of the present invention as defined by the appended claims.

What is claimed is:

1. A device for connecting a camera to a scoping apparatus for viewing and taking photos of an object imaged by the scoping apparatus, the device comprising a case for receiving the camera and an attachment connected to said case and including means for detachably connecting said attachment to an eye-piece of the scopping apparatus in a manner to allow passage of an image from the scoping apparatus through said device to the camera for viewing and taking of photos thereof, wherein said attachment includes means for securely fitting thereof onto the eye-piece, said fitting means including a cylindrical wall having an open end and composed of elastomeric material and having a length of at least about 1 inch to allow secure fitting of said attachment onto the eye-piece, said attachment further including a planar wall integral with said cylindrical wall and closing an other end of said cylindrical wall and connected to said case, wherein said planar wall has an opening for passing of the image to the camera.

2. A device according to claim 1 wherein said case is sized to receive a compact camera.

3. A device according to claim 1 wherein said case is sized to receive a compact phone having the camera.

4. A device according to claim 1 wherein said case is sized to receive a high resolution compact camera.

5. A device according to claim 1 wherein said case is sized to receive a compact phone having a high resolution camera.

6. A device according to claim 1 wherein said cylindrical wall has an inner diameter which is selected from one of about 1¼ inch and about 1½ inch.

7. A device according to claim 1 wherein the device further comprising in combination therewith at least one adapter for receiving between said cylindrical wall and the eye-piece to permit receiving of said attachment on a eye-piece having a smaller diameter than an eye-piece diameter for which said cylindrical wall of said attachment is sized.

8. A device according to claim 1 wherein said case and said attachment are integral with each other.

9. A device according to claim 1 wherein said case has an opening aligned with said planar wall opening, the device further comprising a grommet received in said planar wall opening and said case opening and connecting said attachment to said case in a manner to allow passage of light from the scoping apparatus through said planar wall opening and said case opening to the camera.

10. A device according to claim 1 further comprising a plurality of rivets connecting said attachment to said case.

11. A device according to claim 1 further comprising a scoping apparatus having an eye-piece to which said attachment is attached with said cylindrical wall received over the eye-piece thereby attaching said attachment to the eye-piece and further comprising a camera received in said case.

12. A device according to claim 1 wherein the device further comprises in combination therewith at least one adapter for receiving between said cylindrical wall and the eye-piece to permit receiving of said cylindrical wall of said attachment on an eye-piece having a smaller diameter than an eye-piece diameter for which said cylindrical wall of said attachment is sized, wherein said adapter has a thickness which is generally equal to the difference between the eye-piece diameter and an inner diameter of said cylindrical wall of said attachment and has a generally cylindrical shape with a gap defined by a pair of facing edges which allows said adapter to be pulled apart enough circumferentially to be received on the eye-piece.

13. A device according to claim 1 wherein said cylindrical wall has an inner diameter which is about 1½ inch and wherein the device further comprising in combination therewith at least one adapter for receiving between said cylindrical wall and the eye-piece to permit receiving of said cylindrical wall of said attachment on a eye-piece having a diameter of about 1¼ inch, wherein said adapter has a thickness which is equal to about ¼ inch and has a generally cylindrical shape with a gap defined by a pair of facing edges which allows said adapter to be pulled apart enough circumferentially to be received on the eye-piece.

14. A device according to claim 1 wherein said case is sized to receive a compact phone having the camera.

15. A device for connecting a camera to a scoping apparatus for viewing and taking photos of an object imaged by the scoping apparatus, the device comprising a case for receiving the camera and an attachment connected to said case and including means for detachably connecting said attachment to an eye-piece of the scoping apparatus in a manner to allow passage of an image from the scoping apparatus through said device to the camera for viewing and taking of photos thereof, wherein said means for detachably connecting comprises a cylindrical wall on said attachment, wherein the device further comprising in combination therewith at least one adapter for receiving between said cylindrical wall and the eye-piece to permit receiving of said cylindrical wall of said attachment on a eye-piece having a smaller diameter than an eye-piece diameter for which said cylindrical wall of said attachment is sized, wherein said adapter has a thickness which is generally equal to the difference between the eye-piece diameter and an inner diameter of said cylindrical wall of said attachment and has a generally cylindrical shape with a gap defined by a pair of facing edges which allows said adapter to be pulled apart enough circumferentially to be received on the eye-piece.

16. A device according to claim 15 wherein said cylindrical wall has an open end and is composed of elastomeric material and has a length of at least about 1 inch to allow secure fitting of said attachment onto the eye-piece, said attachment further including a planar wall integral with said cylindrical wall and closing an other end of said cylindrical wall and connected to said case, wherein said planar wall has an opening for passing of the image to the camera.

17. A device according to claim 15 wherein said attachment has a planar wall closing one end of said cylindrical wall and having an opening for passing of the image to the camera and wherein said case has an opening aligned with said planar wall opening, the device further comprising a grommet received in said planar wall opening and said case opening and connecting said attachment to said case in a manner to allow passage of light from the scoping apparatus through said planar wall opening and said case opening to the camera.

18. A device according to claim 15 further comprising a scoping apparatus having an eye-piece to which said attachment is attached with said adapter received between the cylindrical wall and the eye-piece and further comprising a camera received in said case.

19. A device for connecting a camera to a scoping apparatus for viewing and taking photos of an object imaged by the scoping apparatus, the device comprising a case for receiving the camera and an attachment connected to said case and including means for detachably connecting said attachment to an eye-piece of the scoping apparatus in a manner to allow passage of an image from the scoping apparatus through said device to the camera for viewing and taking of photos thereof, wherein said means for detachably connecting comprises a cylindrical wall on said attachment, wherein said cylindrical wall has an inner diameter which is about 1½ inch and wherein the device further comprising in combination therewith at least one adapter for receiving between said cylindrical wall and the eye-piece to permit receiving of said cylindrical wall of said attachment on a eye-piece having a diameter of about 1¼ inch, wherein said adapter has a thickness which is equal to about ¼ inch and has a generally cylindrical shape with a gap defined by a pair of facing edges which allows said adapter to be pulled apart enough circumferentially to be received on the eye-piece.

20. A device according to claim 19 further comprising a scoping apparatus having an eye-piece to which said attachment is attached with said adapter received between the cylindrical wall and the eye-piece and further comprising a camera received in said case.

* * * * *